(12) United States Patent  (10) Patent No.: US 9,295,407 B2
Kolipaka et al.  (45) Date of Patent: Mar. 29, 2016

(54) HYDRAULICALLY-POWERED SYSTEM AND METHOD FOR ACHIEVING MAGNETIC RESONANCE ELASTOGRAPHY

(71) Applicant: OHIO STATE INNOVATION FOUNDATION, Columbus, OH (US)

(72) Inventors: Arunark Kolipaka, Dublin, OH (US); John W. Arnold, New Philadelphia, OH (US); F. Paul Lee, Wooster, OH (US); Richard D. White, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 260 days.

(21) Appl. No.: 13/832,977

(22) Filed: Mar. 15, 2013

(65) Prior Publication Data

US 2013/0303882 A1 Nov. 14, 2013

Related U.S. Application Data

(60) Provisional application No. 61/688,235, filed on May 10, 2012.

(51) Int. Cl.
*A61B 5/055* (2006.01)
*A61B 5/00* (2006.01)
*G01R 33/563* (2006.01)

(52) U.S. Cl.
CPC ............. *A61B 5/0555* (2013.01); *A61B 5/0051* (2013.01); *A61B 5/055* (2013.01); *G01R 33/56358* (2013.01)

(58) Field of Classification Search
CPC ...................... A61B 5/055; G06T 2207/10088; F15B 7/02
See application file for complete search history.

(56) References Cited

U.S. PATENT DOCUMENTS

| 4,472,628 | A | * | 9/1984 | Whitten | 250/227.14 |
|---|---|---|---|---|---|
| 5,540,052 | A | * | 7/1996 | Sieke et al. | 60/540 |
| 7,034,534 | B2 | | 4/2006 | Ehman et al. | |
| 2009/0209847 | A1 | | 8/2009 | Li | |
| 2010/0045289 | A1 | | 2/2010 | Bronskill et al. | |
| 2010/0241012 | A1 | * | 9/2010 | Yin et al. | 600/485 |
| 2011/0025333 | A1 | | 2/2011 | Ehman et al. | |
| 2012/0053450 | A1 | | 3/2012 | Salcudean | |

OTHER PUBLICATIONS

International Search Report and Written Opinion for Application No. PCT/US2013/040272 dated Sep. 5, 2013 (7 pages).
European Patent Office Extended European Search Report for Application No. 13787687.6 dated Dec. 14, 2015 (9 pages).

\* cited by examiner

*Primary Examiner* — Tse Chen
*Assistant Examiner* — Jason Ip
(74) *Attorney, Agent, or Firm* — Michael Best & Friedrich LLP

(57) ABSTRACT

A system for inducing tissue vibration for magnetic resonance elastography is described. The system includes a passive actuator component, a first hose, a second hose, and a driving component. The passive actuator component is positionable proximate to a target tissue and includes a linearly movable piston assembly enclosed in a housing. The driving component includes a fluid pumping system and is configured to alternatingly pump a fluid through the first hose and through the second hose. When fluid is pumped through the first hose, the piston assembly moves in a first linear direction and, when fluid is pumped through the second hose, the piston assembly moves in the opposite direction. The alternating linear movement of the piston assembly induces vibration in the target tissue.

19 Claims, 3 Drawing Sheets

HYDRAULICALLY-POWERED SYSTEM AND METHOD FOR ACHIEVING MAGNETIC RESONANCE ELASTOGRAPHY

RELATED APPLICATIONS

This application claims priority to U.S. Provisional Application No. 61/688,235, filed on May 10, 2012 and titled "HYDRAULICALLY-POWERED SYSTEM AND METHOD FOR ACHIEVING MAGNETIC RESONANCE ELASTOGRAPHY," the entire contents of which are incorporated herein by reference.

BACKGROUND

Embodiments of the invention relate to a non-invasive medical imaging technique, such as magnetic resonance elastography ("MRE"), used in radiology to measure stiffness of soft tissues.

Current MRE technology uses an acoustic driver system, developed by radiology researchers at Mayo Clinic. Current MRE technology, however, is limited to low frequency vibrations (e.g., 100 Hz or less) because it is based on pneumatic actuation. The wavelengths from the low frequency vibrations are smaller than the dimensions of the liver. Therefore, current pneumatic systems can be used to generate stable stiffness maps for the liver, which can be used to diagnose liver diseases, such as liver fibrosis. However, the wavelengths from the lower frequency vibrations are longer than the dimensions of other organs. As a result, current pneumatic systems generating low frequency vibrations cannot be used to generate stable stiffness maps for many organs such as the heart, prostate, pancreas, spleen, eye, etc. This is because the current inversion (a mathematical process to convert wave images to a stiffness map) strategies assume that the waves are propagating in a uniform infinite medium (i.e. the wavelengths are smaller compared to the dimensions of the organs of interest).

SUMMARY

Therefore, embodiments of the invention provide a hydraulically-powered magnetic resonance elastography ("MRE") vibration device used in conjunction with a magnetic resonance imaging ("MRI") scanner that uses an inversion to generate stable stiffness maps for various organs. The vibration device generates high frequency vibrations, up to approximately 1000 Hz, which non-invasively penetrate deeper into tissue than current MRE technology to identify a disease and diagnose the state of the disease for various organs of a human or an animal body.

In one embodiment, the invention provides a hydraulically-powered system used in conjunction with a magnetic resonance imaging ("MRI") device and an inversion to achieve magnetic resonance elastography ("MRE") generated stiffness maps. The hydraulically-powered system includes an application component, a driving component, and a plurality of hoses connecting the application component to the driving component. The application component (also referred to as a passive driver, a passive device, or a passive actuator) includes a piston rod assembly, and is positioned on a surface of a body to cause biological tissues under study to vibrate synchronized with the phase of the MRI signal of the MRI device. The driving component includes a processing unit, a memory storing data and firmware executable by the processing unit, and at least one pump or a combination of a pump and a valve. The driving component is configured to operate the application component at a controlled frequency, amplitude, and phase.

In another embodiment, the invention provides a system for inducing tissue vibration for magnetic resonance elastography. The system includes a passive actuator component, a first hose, a second hose, and a driving component. The passive actuator component is positionable proximate to a target tissue and includes a linearly movable piston assembly enclosed in a housing. The first hose is coupled to the passive actuator component on a first side of the piston assembly and the second hose is coupled to the passive actuator component on the opposite side of the piston assembly. The driving component includes a fluid pumping system and is configured to alternatingly pump a fluid through the first hose and through the second hose. When fluid is pumped through the first hose, the piston assembly moves in a first linear direction and, when fluid is pumped through the second hose, the piston assembly moves in the opposite direction. The alternating linear movement of the piston assembly induces vibration in the target tissue.

In still another embodiment, the invention provides a method of performing magnetic resonance elastography. A passive actuator component is positioned proximate to a target tissue on a patient. The passive actuator includes a linearly movable piston assembly. A fluid is then pumping alternatingly from a driving component through a first hose and a second hose. The first hose is coupled to the passive actuator component on a first side of the piston assembly such that pumping the fluid through the first hose causes the piston assembly to move in a first linear direction. The second hose is coupled to the passive actuator component on a second side of the piston assembly (opposite the first side) such that pumping the fluid through the second hose causes the piston assembly to move in a direction opposite the first linear direction. The alternating linear movement of the piston assembly induces a vibration in the target tissue. MRI data of the target tissue is acquired while the vibration is induced and a stiffness map of the tissue is generated based on the acquired MRI data.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
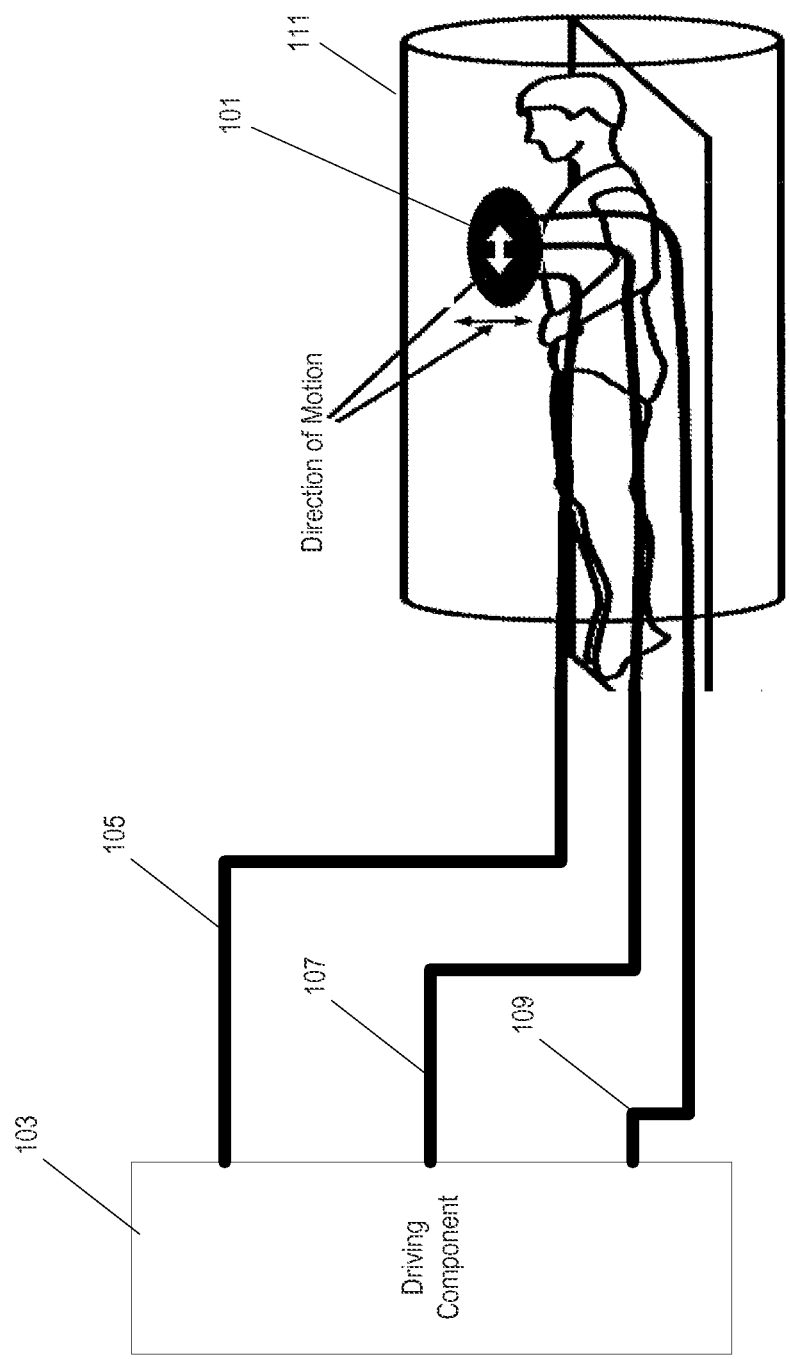
FIG. 1 is an illustration of a hydraulically-powered system used in conjunction with a magnetic resonance imaging ("MRI") device.

FIG. 1 illustrates an example of a hydraulically-powered magnetic resonance elastography ("MRE") system including an application component 101, a driving component 103, and a plurality of hoses 105, 107, 109 connecting the application component 101 to the driving component 103. When a patient is placed in an MRI environment 111, the application component 101 (also referred to as a passive driver, a passive device, or a passive actuator) is adhered to the surface of a patient's body and generates vibrations perpendicular to the tissue surface or shear vibrations along the tissue surface. To prevent interference with the MRI system, the passive driver 101 is constructed of non-metallic/MR compatible components. However, in some constructions, the passive driver 101 includes a limited number of non-ferromagnetic metallic components.

The driving component 103 (also referred to as an active driver) includes pump mechanisms for driving the hydraulic system. As some of these components may be constructed of metal (including ferromagnetic metals), the driving component 103 is positioned outside of the MRI environment/scanning room. As described in detail below, the driving component 103 operates a hydraulic pumping system to control the frequency, displacement amplitude, and phase of the passive driver 101.

The system of FIG. 1 undergoes a three-stage process to produce spatial stiffness maps that estimates stiffness of biological tissues. First, the application component 101 is adhered to the surface of a human body and the driving component 103 causes the application component 101 to vibrate thereby inducing vibration of the biological tissues under study at a controlled frequency, amplitude, and phase. The MRI scanning system 111 is then used to capture data indicative of the transmitted waves in the region of interest ("ROI"). The wave/vibration data captured by the MRI scanning system 111 is then converted to spatial stiffness maps using a mathematical process called inversion. As described further below, the operation of the driving component 103 is coordinated with the phase of the MRI signal of the MRI scanning system 111. For example, the phase of the tissue vibration is synchronized with the phase of the MRI device to obtain optimal imaging. In some constructions, the MRE system can be used to control when to start imaging with the MRI scanner or vice-versa.

Figure 2:
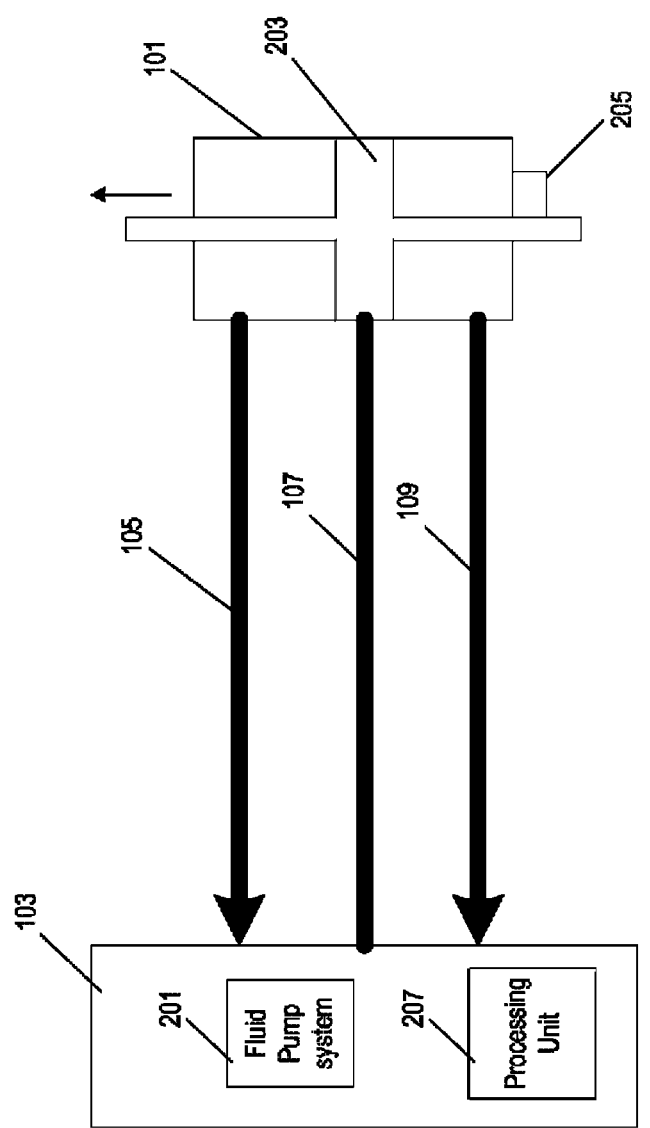
FIG. 2 is a schematic illustration of the system of FIG. 1 including a driving component, an application component, and a plurality of hoses connecting the components.

FIG. 2 illustrates the operational components of the hydraulically powered-vibration system in further detail. The driving component 103 includes at least one pump 201 or a combination of a pump and a valve system to provide flow and pressure of a liquid through the plurality of hoses 105, 107, 109 connected to the passive driver 101. The fluid pumped by the driving component 103 into the passive driver 101 causes a piston 203 to move back and forth periodically to induce vibration of the passive driver 101. The pump 201 of the driving component 103 forces fluid into the passive driver 101 through a first hose 105. The increased pressure on one side of the piston 203 causes the piston to move in a first direction (downward in the example of FIG. 2). At the same time, the fluid pump system 201 of the driving component 103 allows fluid on the opposite side of the piston 203 to drain through the second hose 109 as the piston moves.

The passive driver 101 is equipped with a fiber-optic displacement transducer 205 that measures the position of the piston 203 and provides feedback to the processing unit 207 of the driving component 103. Once the piston 203 reaches a defined displacement, the fluid pump system 201 forces fluid into the passive driver 101 through the second hose 109 and allows fluid to drain through the first hose 105. As a result, the piston 203 is moved in the opposite direction (upward in the example of FIG. 2). Although the example of FIG. 2 includes a displacement sensor 205 that is used to control the operation of the fluid pump system 201, other constructions can utilize other types of sensors to control the operation of the fluid pump system 201. For example, a pressure transducer can be configured to measure the difference in pressure between the first hose 105 and the second hose 109. The fluid pumping system 201 would then be controlled based on these measurements.

The processing unit 207 of the driving component 103 controls the amplitude of the vibration induced through the passive driver 101 by monitoring the displacement of the piston 203 and causing the fluid pump system 201 to reverse the direction of piston movement when a desired amplitude is reached. The frequency of the vibration is controlled by regulating the speed at which the fluid pump 201 forces the liquid into the passive driver 101.

In some embodiments, the fluid pump system 201 of the driving component 103 includes a conventional hydraulic pump that provides consistent flow and pressure to a four-way electro-hydraulic servo valve ("EHSV") to generate a controlled displacement waveform at the application component 101. The valve is electronically controlled by the processing unit to open in alternating directions of flow to send pressurized hydraulic fluid through either the first hose 105 or the second hose 109 to either side of the piston. In some embodiments, the EHSV includes a conventional nozzle flapper-type electro-hydraulic servo valve. In other constructions, the valve is a voice-coil system. A conventional pump that supplies consistent flow and pressure to piezoelectric liquid valves or a modified pump that supplies timed pulses of flow can also be used to generate a controlled displacement waveform at the application component.

As discussed above, the application component 103, shown in FIG. 2, converts supplied hydraulic flow and pressure into displacement of a moveable surface to cause tissue vibration. The application component may take on various embodiments based on established technologies known to those skilled in the art. These include axial hydraulic actuators, such as a cylinder-piston-rod assembly, or chamber-diaphragm-rod assembly types. Other means of actuation, such as rotary actuators or hydraulic motors, could also be used to devise other embodiments of the application component. In the embodiment shown in FIG. 2, the application component comprises a cylinder with a piston and double-rod assembly. The rod is driven under hydraulic power by the piston such that it reciprocates in a fully-reversed linear motion. The rod, in turn, drives the part of the application component that articulates with the patient to generate a vibrational effect at the surface of the patient's body. It should be clear to those familiar with hydraulic technologies and skilled in the art that this vibrational effect could be generated by hydraulic devices of various constructions and designs. As noted above, the application component 101 in this example is non-metallic (e.g., includes plastic components), which makes it MR compatible. However, in some embodiments, the application component 101 includes at least some metallic components.

As described above, a plurality of hoses distributes a non-compressible liquid between the passive actuator 101 and the driving component 103. Pressurized hydraulic fluid supplied at the first hose 105 moves the piston and rod assembly 203 in the first direction (e.g., downward). Pressurized hydraulic fluid supplied at the second hose 109 moves the piston and rod assembly 203 in the opposite direction (e.g., upward). This motion is transferred to the surface of the passive actuator 101 to generate tissue vibrations. A third hose 107 is a low pressure return hose that allows leakage flow to return to a fluid reservoir of the driving component 103. The return hose 107 bleeds air from the lines and the cylinder internal volumes.

By using a virtually incompressible media (e.g., liquid) to drive the passive actuator 101, the hydraulically-powered system provides many advantages over pneumatic means of generating tissue vibration. For example, pneumatic systems are limited by gas (e.g., air) compliance to a frequency on an order of 100 Hz or less. This frequency limitation limits the resolution of the MRE to the imaging of smaller tissue structures. A liquid fluid means of driving the application head does not have this limitation as the media used to convey flow and pressure has negligible compliance. Therefore, higher transmitted frequencies are possible using the hydraulically-powered vibration device.

In addition, because of the virtual incompressibility of liquids, the performance of the system using the hydraulically-powered vibration device can be predicted with sufficient accuracy to allow the phase of the tissue vibrations to be adjusted to the phase of the applied MRI, which provides optimal imaging. The use of virtually incompressible media also makes it possible to generate higher forces that overcome attenuation of the transmitted energy, which results in the delivery of higher energies to the tissue of interest. Furthermore, because higher power can be transmitted by liquid fluidic means, flexibility in the design of the passive actuator 101 is accommodated. In particular, passive actuators can be implemented that transmit either longitudinal vibrations (i.e., perpendicular to the tissue surface) or shear vibrations (i.e., along the tissue surface). In general, the hydraulically-powered vibration device provides higher-frequency, phase-tuned tissue vibration that provides not only greater imaging resolution due to higher frequency vibration but also better clarity due to phase control.

In some embodiments, the fluid used in the vibration device can be doped with a contrast agent (e.g., super paramagnetic iron oxide) to suppress a signal provided by the fluid in the MRI scanner that can create possible artifacts in the resulting images. Similarly, the field of view can be limited by avoiding the driver or saturation bands that dephase the signal from the fluid to prevent these artifacts. Also, in some embodiments, the passive actuator can be flexible, and can be properly sealed to prevent any fluid leaks.

Figure 3:
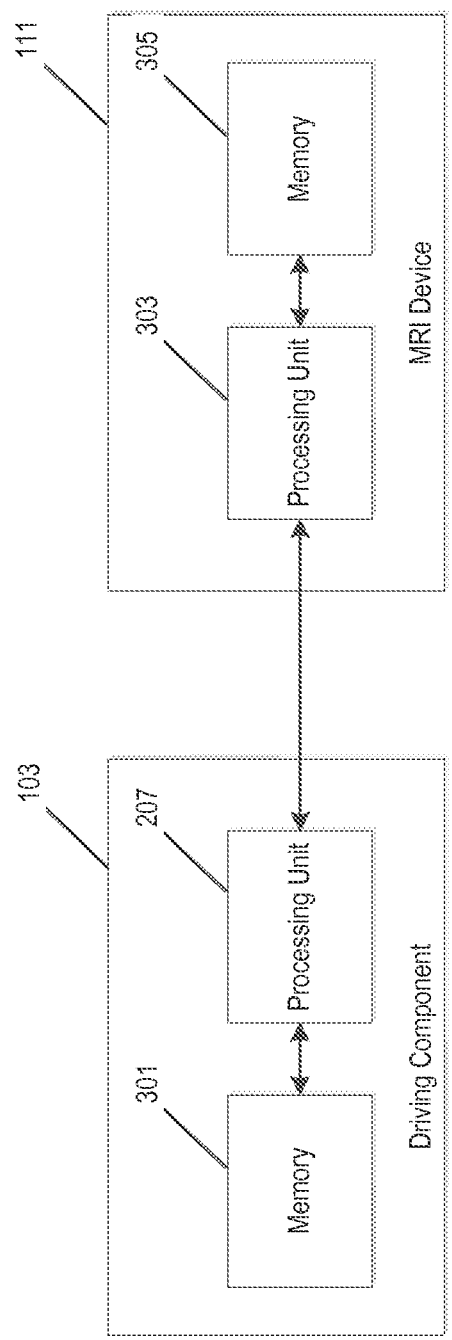
FIG. 3 is a schematic illustration of the driving component of FIG. 2 interfacing with the MRI device.

To further optimize the quality of vibration data acquired by the MRI scanning system 111, the driving component 103 is configured to communication (bidirectional or unidirectional) with the controller of the MRI scanning system 111 as illustrated in FIG. 3. The driving component 103 includes a processing unit (such as a microcontroller) and a memory storing executable instructions and data that, when executed by the processing unit, cause the driving component to operate the fluid pump system and communicate with the MRI scanning system 111. The MRI scanning system also includes a processing unit 303 and a memory 305.

The communication between the driving component 103 and the MRI scanning system 111 allows the vibration to be coordinated with and paced by the pulse sequencing of the MRI scanning system 111 or vice versa. As discussed above, the frequency and amplitude of the induced tissue vibration can be controlled by adjusting the speed at which fluid is pumped into the passive actuator 101 and the desired displacement of the piston and rod assembly 203, respectively. Conversely, in some constructions, the pulse sequencing of the MRI system 111 is controlled based on the frequency and amplitude of the vibrations caused by the driving component 103.

Thus, the invention provides, among other things, a hydraulic system for inducing vibrations in target tissue so that spatial stiffness maps can be generated using magnetic resonance elastography. Various features and advantages of the invention are set forth in the following claims.

What is claimed is:

1. A system for inducing tissue vibration for magnetic resonance elastography, the system comprising:
a passive actuator component positionable proximate to a target tissue, the passive actuator component including a linearly movable piston assembly enclosed in a housing such that alternating linear movement of the linearly movable piston causes vibration of the passive actuator component and induces vibration of the target tissue when the passive actuator component is positioned proximate to the target tissue;
a first hose coupled to the passive actuator on a first side of the piston assembly;
a second hose coupled to the passive actuator on a second side of the piston assembly opposite the first side; and
a driving component including a fluid pump, the driving component configured to alternatingly pump a fluid through the first hose causing the piston assembly to move in a first linear direction and pump the fluid through the second hose causing the piston assembly to move in a second linear direction, the second linear direction being opposite to the first linear direction,
wherein the passive actuator component further includes a displacement sensor configured to provide a signal to the driving component indicative of a linear position of the piston assembly,
wherein the driving component is configured to
switch from pumping the fluid through the first hose to pumping the fluid through the second hose when the signal from the displacement sensor indicates that the linear position of the piston assembly in the first linear direction meets or exceeds a displacement threshold, and
switch from pumping the fluid through the second hose to pumping the fluid through the first hose when the signal from the displacement sensor indicates that the linear position of the piston assembly in the second linear direction meets or exceeds the displacement threshold, and
wherein the displacement sensor includes a fiber-optic displacement transducer.

2. The system of claim 1, wherein the driving component is further configured to
passively allow fluid to drain from the passive actuator through the second hose when fluid is being pumped to the passive actuator through the first hose, and
passively allow fluid to drain from the passive actuator through the first hose when fluid is being pumped to the passive actuator through the second hose.

3. The system of claim 1, wherein the passive actuator is constructed of only non-metallic components.

4. The system of claim 1, wherein the passive actuator is constructed of only non-ferromagnetic components.

5. The system of claim 1, wherein the passive actuator is positionable within an MRI environment and the driving component is positioned outside of the MRI environment.

6. The system of claim 1, wherein the driving component is further configured to adjust a frequency of the induced tissue vibration by changing the frequency of the fluid pump system.

7. The system of claim 1, wherein the driving component is further configured to adjust an amplitude of the induced tissue vibration by increasing a displacement of the piston assembly by changing the flow rate of the fluid pump system.

8. The system of claim 1, wherein the driving component is configured to induce tissue vibration at a frequency greater than 100 Hz.

9. The system of claim 1, wherein the driving component further includes a valve coupled to the fluid pump, the first hose, and the second hose to controllably alternate a supply of pressurized fluid from the fluid pump to each respective side of the piston assembly by alternatingly providing fluid from the fluid pump to the first hose and to the second hose, and wherein the driving component is further configured to
- electronically receive a message from an MRI scanning system indicative of a desired change in at least one of an amplitude and a displacement of the vibration induced by the passive actuator component, wherein the message is based on image data acquired by the MRI scanning system, and
- adjust at least one of the frequency and the amplitude of the induced tissue vibration by the driving component to synchronize to the encoding gradients of the MRI scanning system, wherein the driving component is configured to adjust the frequency of the induced tissue vibration by increasing the frequency at which the valve shifts to alternate the supply of pressurized fluid to the respective sides of the piston assembly of the passive actuator component, and wherein the driving component is configured to adjust the amplitude of the induced tissue vibration by adjusting a maximum displacement of the piston assembly.

10. The system of claim 1, wherein the driving component is further configured to
- electronically receive a message from an MRI scanning system indicating when the induced tissue vibration should begin, and
- begin inducing the tissue vibration according to the message from the MRI scanning system.

11. The system of claim 1, wherein the driving component is further configured to electronically transmit a message to the MRI scanning system indicating when the MRI scanning system is to begin acquiring data, wherein the message is based on the induced tissue vibration.

12. The system of claim 1, wherein the first linear direction is perpendicular to a skin surface of the patient, and wherein the induced vibration is a longitudinal vibration.

13. The system of claim 1, wherein the first linear direction is parallel to a skin surface of the patient, and wherein the induced vibration is a shear vibration.

14. A method of performing magnetic resonance elastography, the method comprising:
- positioning a passive actuator component proximate to a target tissue on a patient, the passive actuator including a linearly movable piston assembly enclosed in a housing;
- alternatingly pumping a fluid from a driving component through a first hose, the first hose being coupled to the passive actuator component on a first side of the piston assembly, wherein pumping the fluid through the first hose causes the piston assembly to move in a first linear direction and pumping a fluid from the driving component through a second hose, the second hose being coupled to the passive actuator component on a second side of the piston assembly opposite the first side, wherein pumping the fluid through the second hose causes the piston assembly to move in a second linear direction opposite the first linear direction, and wherein the linear movement of the piston assembly alternatingly in the first linear direction and the second linear direction induces vibration in the target tissue, and wherein alternating the linear movement of the piston assembly causes vibration of the passive actuator component and induces vibration of the target tissue;
- acquiring MRI data of the target tissue while vibration of the target tissue is induced; and
- generating a stiffness map of the tissue based on the acquired MRI data,
- wherein the act of alternatingly pumping a fluid from a driving component further includes:
- receiving a signal from a displacement sensor indicative of the linear displacement of the piston assembly, the displacement sensor including a fiber optic displacement transducer,
- switching from pumping the fluid through the first hose to pumping the fluid through the second hose when the signal from the displacement sensor indicates that the linear displacement of the piston assembly in the first linear direction meets or exceeds a displacement threshold, and
- switching from pumping the fluid through the second hose to pumping the fluid through the first hose when the signal from the displacement sensor indicates that the linear displacement of the piston assembly in the second linear direction meets or exceeds the displacement threshold.

15. The method of claim 14, further comprising generating a phase image of the vibration of the tissue based on the MRI data.

16. The method of claim 15, wherein the stiffness map of the tissue is generated by performing an inversion on the phase image MRI data.

17. The method of claim 14, further comprising regulating the amplitude and frequency of the vibration induced in the target tissue by regulating a displacement of the piston assembly and a frequency at which fluid pump flow is alternately diverted to the first hose and the second hose of the passive actuator component.

18. The method of claim 14, further comprising regulating the amplitude of the vibration induced in the target tissue by increasing or decreasing the displacement threshold.

19. The method of claim 14, further comprising:
- receiving a feedback message from an MRI phase data acquisition controller; and
- regulating at least one of a frequency and an amplitude of the induced vibration in the target tissue based on the feedback message from the MRI phase data acquisition controller.

* * * * *